United States Patent [19]

Iqbal

[11] 4,366,312
[45] Dec. 28, 1982

[54] METAL COMPLEXES OF ISOINDOLINAZINES, PROCESS FOR THEIR PREPARATION AND USE

[75] Inventor: Abul Iqbal, Ettingen, Switzerland

[73] Assignee: Ciba-Geigy Corporation, Ardsley, N.Y.

[21] Appl. No.: 242,004

[22] Filed: Mar. 9, 1981

[30] Foreign Application Priority Data

Mar. 13, 1980 [CH] Switzerland .................. 1978/80

[51] Int. Cl.³ .................................. C07D 209/14
[52] U.S. Cl. ........................ 542/417; 106/288 Q; 544/225; 546/6; 546/7; 548/105; 548/106; 548/403; 548/471; 548/466; 548/472
[58] Field of Search .............. 542/417; 544/225; 548/105, 106; 546/6, 7; 260/326.1

[56] References Cited

U.S. PATENT DOCUMENTS

| | | | |
|---|---|---|---|
| 3,867,404 | 2/1975 | von der Crone et al. | 542/417 |
| 3,974,149 | 8/1976 | L'Eplattenier et al. | 542/417 |
| 4,016,159 | 4/1977 | Unttel et al. | 544/225 |
| 4,022,770 | 5/1977 | L'Eplattenier et al. | 542/417 |
| 4,024,132 | 5/1977 | L'Eplattenier et al. | 542/417 |
| 4,111,947 | 9/1978 | L'Eplattenier et al. | 542/417 |
| 4,132,708 | 1/1979 | L'Eplattenier et al. | 542/417 |
| 4,237,286 | 12/1980 | L'Eplattenier et al. | 544/225 |
| 4,237,292 | 12/1980 | L'Eplattenier et al. | 544/225 |
| 4,237,293 | 12/1980 | L'Eplattenier et al. | 544/225 |
| 4,296,030 | 10/1981 | Lang et al. | 544/225 |

OTHER PUBLICATIONS

CA, 58, 5546g, 7863e, (1963).

*Primary Examiner*—Arthur P. Demers
*Attorney, Agent, or Firm*—Luther A. R. Hall

[57] ABSTRACT

1:1 metal complexes of azines of the formula

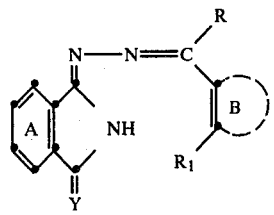

(1)

in which the ring A can be further substituted, R is an H atom or an alkyl or aryl group, B is an isocyclic or heterocyclic aromatic radical or an alicyclic radical, $R_1$ is the OH or SH group and Y is a radical of the formula

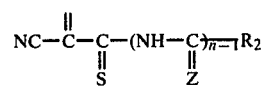

(2)

in which Z is an O or S atom, n is the number 1 or 2 and $R_2$ is an alkyl, aralkyl, cycloalkyl or aryl radical or an amino group which is unsubstituted or substituted by an alkyl, cycloalkyl, aralkyl or aryl radical.

In plastics and surface coatings, the novel pigments give intense pure orange to violet colorations with good fastness properties.

5 Claims, No Drawings

METAL COMPLEXES OF ISOINDOLINAZINES, PROCESS FOR THEIR PREPARATION AND USE

The invention relates to 1:1 metal complexes of isoindolinazines of the formula

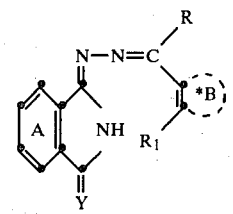
(1)

in which the ring A can be further substituted, R is an H atom or an alkyl or aryl group, B is an isocyclic or heterocyclic aromatic radical or an alicyclic radical, $R_1$ is the OH or SH group and Y is a radical of the formula

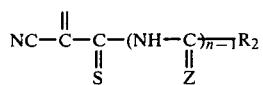
(2)

in which Z is an O or S atom, n is the number 1 or 2 and $R_2$ is an alkyl, aralkyl, cycloalkyl or aryl radical or an amino group which is unsubstituted or substituted by an alkyl, cycloalkyl, aralkyl or aryl radical.

As substituents in the benzene ring A, the isoindolinonazines (sic) of the formula (1) can contain halogen atoms, for example 2–4 chlorine atoms, 1–2 alkyl or alkoxy groups having 1–4 C, a phenyl, phenoxy, nitro or benzoylamino group or an alkanoylamino group having 2–6 C, but they are preferably unsubstituted.

R is, for example, a phenyl or naphthyl radical and preferably an H atom or an alkyl group having 1–4 C, in particular the methyl group.

B is, for example, a phenylene or naphthylene radical, but especially a 5–6-membered heterocyclic ring, which may or may not be fused, containing an N, O, or S atom in the β-position to the C* atom, and, if desired, a further N atom in the ring. B is, for example, a pyrazole, pyrimidine, quinoline or coumarin ring. $R_1$ is preferably the hydroxyl group. An alicyclic radical B is preferably a cyclohexyl radical.

An alkyl radical $R_2$ preferably has 1–4 C. A cycloalkyl radical $R_2$ is in particular the cyclohexyl radical. An aryl radical $R_2$ is, for example, a naphthyl and especially phenyl radical. An amino group $R_2$ is preferably substituted by an alkyl group having 1–4 C, a cyclohexyl group or a phenyl or benzyl group.

Preferred metal complexes are those of the formula

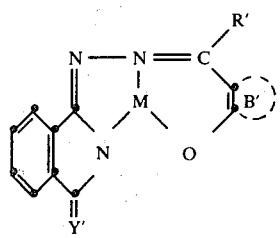
(3)

in which M is nickel or copper, R' is H or methyl, B' is a pyrazole, pyrimidine, quinoline or coumarin radical and Y' is a radical of the formula

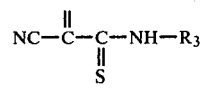
(4)

in which $R_3$ is an H atom, an alkyl group having 1–4 C or a radical of the formula

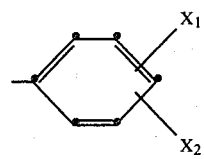
(5)

in which $X_1$ is an H, chlorine or bromine atom, a nitro, trifluoromethyl, carbamoyl or sulfamoyl group, an alkyl, alkoxy or alkylsulfamoyl group having 1–4 C, an alkanoylamino, alkylcarbamoyl or alkoxycarbonyl group having 2–6 C, or a phenoxy, phenylcarbamoyl or phenylsulfamoyl group which is unsubstituted or substituted by chlorine or bromine atoms or methyl groups, and $X_2$ is an H, chlorine or bromine atom or an alkyl or alkoxy group having 1–4 C.

Metal complexes which are also preferred are those of the formula (3) in which Y' is a radical of the formula

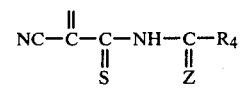

in which Z is O or S and $R_4$ is an alkyl group having 1–4 C, a cyclohexyl or benzyl group or a group of the formula (5).

The formulae (1) and (3) represent only one of the various isomeric forms.

The metal complexes of the formula (1) are obtained by (a) treating an azine of the formula (1) with metal donors or (b) heating a hydrazone of the formula

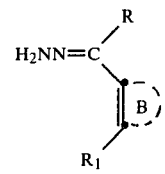
(6)

in which R, $R_1$ and B are as defined, with an isoindolinone of the formula (7)

or an amino-isoindolenine of the formula

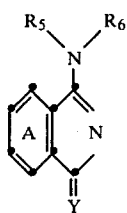 (8)

in which $R_5$ and $R_6$ are H atoms or alkyl, aryl or heteroaryl groups, or $R_5$ and $R_6$, together with the N atom, are a heterocyclic 5- or 6-membered ring, and A and Y are as defined, in the presence of metal donors, in a polar organic solvent.

Alkyl radicals $R_5$ and $R_6$ preferably have 1-6 C. An aryl radical $R_6$ is preferably a phenyl radical which is unsubstituted or substituted by chlorine atoms or alkyl or alkoxy groups having 1-4 C.

The azines of the formula (1) are obtained, for example, by the process described in British Pat. No. 1,467,595, wherein a hydrazone of the formula (6) is condensed with an amino-isoindolenine of the formula (8) in which A and Y are as defined and $R_5=R_6=H$.

The compound of the formula (8) is obtained by condensing the methine-imino-isoindolenine of the formula

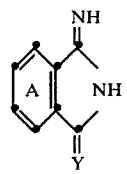 (9)

with an amine of the formula

in which A, Y, $R_5$ and $R_6$ are as defined. The compound of the formula (9) is in turn obtained by reacting the amino-imino-isoindoline of the formula

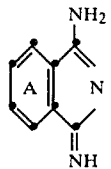 (10)

with a compound of the formula

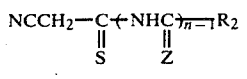 (11)

in which A, Z, n and $R_2$ are as defined. Examples of amino-imino-isoindolinone (sic) are those listed on page 5 of British Pat. No. 1,465,595.

Examples of compounds of the formula (11) are: $NCCH_2CSCH_3$, $NCCH_2CSC_2H_5$, $NCCH_2CSCH_2CH_2CH_3$, $NCCH_2CSCH(CH_3)_3$, $NCCH_2CS(CH_2)_3CH_3$, $NCCH_2CSCH_2CH(CH_3)_2$, $NCCH_2CSCH_2C_6H_5$, $NCCH_2CS$-cyclohexyl, $NCCH_2$—CS-phenyl, $NCCH_2CS$—(o-, m- or p)-chlorophenyl, $NCCH_2CSNH_2$, $NCCH_2CSNHCH_3$, $NCCH_2CSNHC_2H_5$, $NCCH_2CSNHCH(CH_3)_2$, $NCCH_2CSNH(CH_2)_3CH_3$, $NCCH_2CSNHCH_2(CH_3)_2$, $NCCH_2$—CSNH-cyclohexyl, $NCCH_2CSNHCH_2C_6H_5$, $NCCH_2$—CSNH-phenyl, $NCCH_2$—CSNH—(o-, m- or p)-chlorophenyl, $NCCH_2CSNH$—(o-, m- or p)-methylphenyl, $NCCH_2CSNH$—(o-, m- or p)-methoxyphenyl, $NCCH_2CSNH$—α-naphthyl, $NCCH_2CSNHCOCH_3$, $NCCH_2CSNHCO$-phenyl, $NCCH_2CSNHCONHC_2H_5$, $NCCH_2CSNHCONHC_6H_5$ and $NCCH_2CSNHCSNHC_6H_5$.

The N-substituted thiocarbamoylacetonitrile derivatives can be prepared, inter alia, by the known process (A. D. Grabenko et at., Zh. Obshch. Khim. 32 (1962) 2,248, c.f. Chem. Abstr. 58, 5546g, 7863e) of reacting cyanoacetic acid esters with the corresponding isothiocyanate, followed by hydrolysis and decarboxylation.

The hydrazones of the formula (6) are obtained by the known process of reacting the oxo compound of the formula

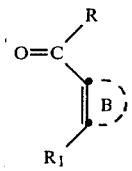

in which R, $R_1$ and B are as defined, or its imines or preferably anils, with hydrazine hydrate.

Examples of oxo compounds of the formula (11) are the aldehydes and ketones listed on pages 11 and 12 of British Pat. No. 1,467,595 and also 2-formyl-5,5-dimethylcyclohexane-1,3-dione and 1-phenyl-3-methyl-4-formyl-5-mercapto-pyrazole.

The isoindolinones of the formula (7) used as starting materials for method (b) are obtained by reacting the imino-isoindolinones of the formula

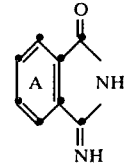

in which A is as defined, a phthalodinitrile or an o-cyanobenzoic acid ester with compounds of the formula (10) by known processes.

The metal donors used are preferably salts of zinc, cadmium, manganese, cobalt and iron, but especially of copper and nickel, or of mixtures of these metals. The formates, acetates or stearates of these metals are advantageously used.

The reactions take place in a polar solvent, in particular one of a hydrophilic nature, for example an amide, such as dimethylformamide, formamide, dimethylacetamide or N-methylpyrrolidone, or also dimethyl sulfoxide, acetonitrile or an alcohol, for example ethylcellosolve. It is also possible to use a mixture of polar solvents.

The reaction temperature is advantageously between 100° to 200° C.

The metal complex obtained is isolated in the customary manner by filtration. The material on the suction filter is washed thoroughly with solvent. It is obtained in excellent yield and purity and can be used without further purification, in finely divided form, for colouring high-molecular organic material, for example cellulose ethers and esters, such as ethylcellulose, acetylcellulose and nitrocellulose, polyamides, polyurethanes or polyesters, and natural resins or synthetic resins, for example aminoplasts, in particular urea/formaldehyde and melamine/formaldehyde resins, alkyd resins, phenoplasts, polycarbonates, polyolefins, such as polystyrene, polyvinyl chloride, polyethylene, polypropylene, polyacrylonitrile and polyacrylic acid esters, thermoplastic or curable acrylic resins, rubber, casein, silicone and silicone warts (sic), individually or in mixtures. The high-molecular compounds mentioned can be in the form of plastic masses or melts or in the form of spinning solutions, surface coatings or printing inks. Depending on the intended use, it proves advantageous to use the novel pigments as toners or in the form of preparations.

The pigment can be employed in the form in which it is obtained in the synthesis, or in a lightly ground form, in which case it produces opaque final colorations. However, it can also be subjected to intensive grinding, in which case transparent final colorations, for example intensely coloured metallic-effect coatings, are obtained.

Pastes of the pigments in surface coatings are distinguished by favourable flow properties.

The colorations obtained, for example in plastics, fibres and surface coatings, are distinguished by high colour intensity, high purity of colour shade, good dispersibility and good fastness to overcoating, migration, heat, light and weather, and also by a good gloss.

In the following examples, percentages are by weight and degrees are degrees centigrade.

Example 1

12.21 g (0.04 mol) of 1-(cyano-phenylthiocarbamoyl-methylene)-3-oxo-isoindoline, prepared from 1-imino-3-oxo-isoindoline and cyanothioacetanilide, 10.03 g (0.04 mol) of 1-p-chlorophenyl-3-methyl-4-hydrazinomethylene-5-pyrazolone and 10.5 g (0.042 mol) of nickel acetate.4H$_2$O are successively suspended in 400 ml of dimethylformamide. The resulting suspension is heated to 120° C. and stirred at the same temperature for 2 hours. The mixture is then cooled to 80° C. and the metal complex obtained as a thick precipitate is filtered off. The material on the suction filter is washed with dimethylformamide and ethanol and dried in vacuo at 80° C. In this way, 22.2 g (93.3% of theory) of the 1:1 nickel complex of the formula

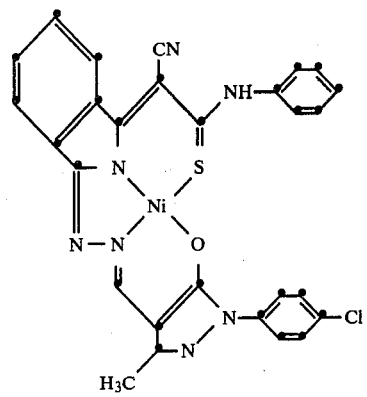

are obtained.

| Microanalysis: | C$_{28}$H$_{18}$ClN$_7$OSNi | | MW 594.72 | | |
|---|---|---|---|---|---|
| calculated* | C 54.8% | H 3.3% | N 16.0% | S 5.23% | Ni 9.58% |
| found | C 54.7% | H 3.1% | N 16.5% | S 5.5% | Ni 9.43% |

*taking into account the amount of H$_2$O found, i.e. 2.9%

The above metal complex pigment colours plastics and surface coatings in red shades with excellent fastness properties.

Example 2

1.95 g (0.008 mol) of 2-anilinomethylene-5,5-dimethylcyclohexane-1,3-dione are dissolved in 50 ml of dimethylformamide and treated with 0.4 ml of hydrazine hydrate and the mixture is then stirred for 1 hour at room temperature. 2.1 g (0.0084 mol) of nickel acetate.4H$_2$O are added and the mixture is warmed to 60° C. The resulting suspension is treated with 2.44 g (0.008 mol) of 1-(cyano-N-phenylthiocarbamoylmethylene)-3-isoindolinone, warmed to 120° C. and stirred at the same temperature for 1 hours. After cooling the reaction mixture to 80° C., the metal complex which has precipitated out is filtered off, washed with dimethylformamide and ethanol and finally dried overnight at 80° C. in vacuo. 3.5 g (83% of theory) of a red pigment of the composition

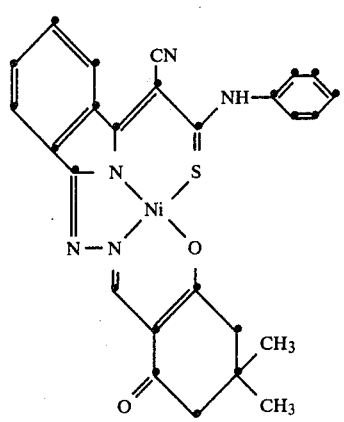

are obtained.

| Microanalysis: | C$_{26}$H$_{21}$N$_5$O$_2$SNi | MW 526 |
|---|---|---|
| calcu- | | |

| -continued | | | | | |
|---|---|---|---|---|---|
| Microanalysis: | $C_{26}H_{21}N_5O_2SNi$ | MW 526 | | | |
| ated: | 59.34% C | 4.02% H | 13.31% N | 6.09% S | 11.16% Ni |
| found: | 59.2% C | 4.2% H | 13.5% N | 6.5% S | 11.3% Ni |

The above metal complex colours plastics and surface coatings in orange shades with excellent fastness properties.

Example 3

If the procedure of Example 2 is repeated, except that 1-(cyano-thiocarbamoylmethylene)-3-isoindolinone is used in place of the 1-(cyano-N-phenylthiocarbamoylmethylene)-3-isoindolinone, 2.3 g (64% of theory) of an orange-red complex of the composition

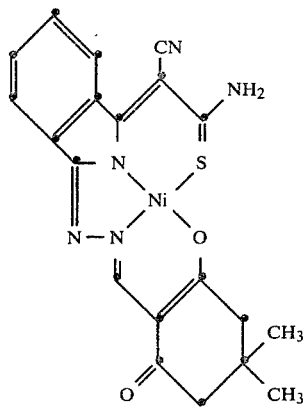

are obtained.

| Microanalysis: | $C_{20}H_{17}N_5O_2SNi$ | MW 450 | | | |
|---|---|---|---|---|---|
| calculated: | 53.36% C | 3.81% H | 15.56% N | 7.12% S | 13.04% Ni |
| found: | 53.5% C | 3.8% H | 15.8% N | 7.1% S | 13.0% Ni |

The above pigment colours plastics and surface coatings in orange shades with a high level of fastness.

Example 4

1.72 g (0.007 mol) of 1-phenyl-3-carbamoyl-4-hydrazinomethylene-pyrazol-5-one are suspended with 1.83 g (0.00735 mol) of nickel acetate.4H$_2$O in 30 ml of N-methylpyrrolidone and the suspension is then warmed to 60° C. 2.14 g (0.007 mol) of 1-(cyano-N-phenylthiocarbamoylmethylene)-3-isoindolinone are added and the mixture is heated to 115° C. and left to react at the same temperature for 2 hours. It is then cooled to 80° C. and the product which has precipitated out is filtered off. After washing with N-methylpyrrolidone and ethanol and drying at 80° C. in vacuo, 2.6 g (67% of theory) of a wine-red metal complex of the structure

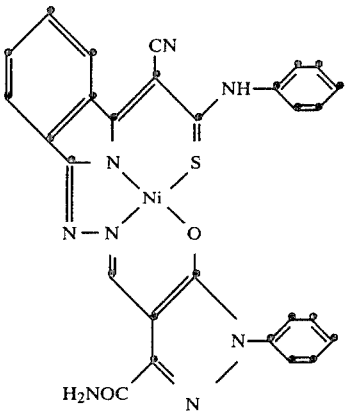

are obtained.

| Microanalysis: | $C_{28}H_{18}N_8O_2SNi$ | MW 589 | | | |
|---|---|---|---|---|---|
| calculated: | 57.07% C | 3.08% H | 19.01% N | 5.44% S | 9.96% Ni |
| found: | 57.2% C | 3.2% H | 19.2% N | 5.3% S | 9.8% Ni |

When incorporated into plastics and surface coatings, the above pigment produces red shades with excellent fastness properties.

Example 5

1.3 g (0.006 mol) of 2,4-dihydroxy-3-acetylquinoline-hydrazone and 1.57 g (0.0063 mol) of nickel acetate. 4H$_2$O are suspended in 50 ml of dimethylformamide. After warming to 60° C., 1.82 g (0.006 mol) of 1-(cyano-thiocarbamoylmethylene)-5,6-dichloro-3-isoindolinone are added, with stirring, and the mixture is heated further to 105° C. and left to react for 2 hours at the same temperature. It is then cooled to 80° C. and the metal complex which has precipitated out is filtered off, washed with dimethylformamide and ethanol and dried overnight at 80° C. in vacuo. 3.2 g (96% of theory) of a red metal complex of the composition $C_{22}H_{12}Cl_2N_6O_2SNi$ and the structure

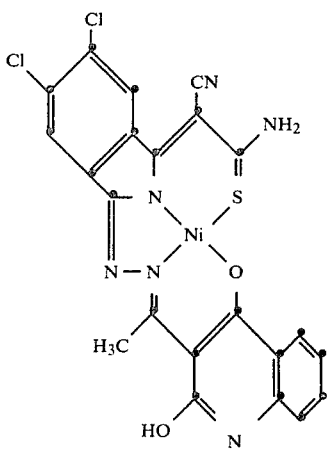

are obtained.

| Microanalysis: | $C_{22}H_{12}Cl_2N_6O_2SNi$ | MW 554 | | | |
|---|---|---|---|---|---|
| calculated: | 47.69% C  2.18% H | 15.17% N  5.79% S | 12.80% Cl | 10.60% Ni |
| found: | 47.2% C  2.4% H | 15.3% N  5.5% S | 12.4% Cl | 10.3% Ni |

The above pigment colours plastics and surface coatings in bluish red shades with excellent fastness properties.

Example 6

0.4 ml of hydrazine hydrate (0.008 mol) is added to a solution of 2.35 g (0.008 mol) of 1-phenyl-3-methyl-4-anilinomethylene-5-thiopyrazolone in 50 ml of dimethylformamide and the mixture is stirred at room temperature for 1 hour. After the further addition of 2.1 g (0.0084 mol) of nickel acetate.4H$_2$O, the reaction (sic) mixture is warmed to 60° C. and then treated with 2.44 g (0.008 mol) of 1-(cyano-N-phenylthiocarbamoylmethylene)-3-isoindolinone. The mixture is left to react at 120° C. for 1 hour and then cooled to 80° C. and filtered. The filtration residue is washed with dimethylformamide and ethanol and dried overnight at 80° C. in vacuo. 2.2 g (48% of theory) of a reddish brown metal complex of the composition

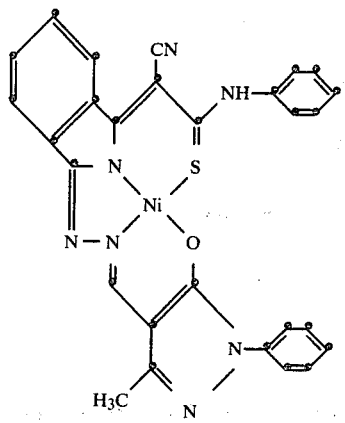

are obtained.

| Microanalysis: | $C_{28}H_{19}N_7S_2Ni$ | MW 576 | |
|---|---|---|---|
| calculated: | 58.35% C  3.32% H | 17.01% N  11.13% S | 10.19% Ni |
| found: | 57.8% C  3.4% H | 17.1% N  11.1% S | 10.3% Ni |

Examples 7–35

Analogously to Examples 1–6, further 1:1 nickel complexes are obtained by condensing the hydrazone of the oxo compounds indicated in column 2 of the table with the isoindolinone of the formula

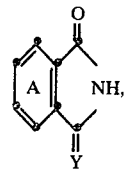

the latter having been obtained by condensing the 3-imino-isoindolinone mentioned in column 3 with the compounds YH$_2$ listed in column 4. Column 5 gives the shade in PVC.

TABLE 1

| Example No. | Oxo compound | Isoindolinone | YH$_2$ | Shade in PVC |
|---|---|---|---|---|
| 7 | 3-Acetyl-2,4-dihydroxy-quinoline | 3-Imino-isoindolinone | Cyanomethylthiocarb-p-chloroanilide | red |
| 8 | 3-Acetyl-2,4-dihydroxy-quinoline | 3-Imino-isoindolinone | Cyanomethylthiocarb-p-toluidide | red |
| 9 | 3-Acetyl-2,4-dihydroxy-quinoline | 3-Imino-isoindolinone | Cyanomethylthiocarb-p-anisidide | red |
| 10 | 1-p-Chlorophenyl-3-methyl-4-formyl-pyrazal-5-one (sic) | 3-Imino-isoindoline | Cyanomethylthiocarbanilide | red |
| 11 | 3-Acetyl-2,4-dihydroxy-quinoline | 3-Imino-isoindoline | Cyanomethylthiocarbanilide | red |
| 12 | 3-Acetyl-2,4-dihydroxy-quinoline | 3-Imino-isoindoline | Cyanomethylthiocarbanilide | red |
| 13 | 5-Acetyl-2,4,6-di-hydroxy-pyrimidine | 3-Imino-isoindoline | Cyanomethylthiocarbanilide | orange |
| 14 | 3-Acetyl-4-hydroxy-coumarin | 3-Imino-isoindoline | Cyanomethylthiocarbanilide | red |
| 15 | 1-(2',4',6'-trichloro-phenyl)-3-methyl-4-formyl-pyrazol-5-one | 3-Imino-isoindolinone | Cyanomethylthiocarbanilide | red |
| 16 | 1-(3',4'-dichloro-phenyl)-3-methyl-4-acetyl-pyrazol-5-one | 3-Imino-isoindolinone | Cyanomethylthiocarbanilide | red |
| 17 | 3-Acetyl-2,4-dihydroxy | 3-Imino-isoindolinone | Cyanomethylthiocarbanilide | red |

TABLE 1-continued

| Example No. | Oxo compound | Isoindolinone | YH₂ | Shade in PVC |
|---|---|---|---|---|
| 18 | 5-Acetyl-2,4,6-tri-hydroxy-pyrimidine quinoline | 3-Imino-isoindolinone | Cyanomethylthiocarbanilide | orange |
| 19 | 3-Acetyl-4-hydroxy-coumarin | 3-Imino-isoindolinone | Cyanomethylthiocarbanilide | red |
| 20 | 1-Phenyl-5-acetyl-4,6-dihydroxy-pyrimidine | 3-Imino-isoindolinone | Cyanomethylthiocarbanilide | red |
| 21 | 3-Acetyl-2,4-dihydroxy-quinoline | 3-Imino-isoindolinone | Cyanomethylthiocarb-butylamide | red |
| 22 | 3-Acetyl-4-hydroxy coumarin | 3-Imino-isoindolinone | Cyanomethylthiocarb-butylamide | orange |
| 23 | 3-Acetyl-4-hydroxy coumarin | 3-Imino-isoindolinone | Cyanomethylthiocarb-butylamide | scarlet |
| 24 | 1-p-Chlorophenyl-3-methyl-4-acetyl-pyrazol-5-one | 3-Imino-isoindolinone | Cyanomethylthiocarb-butylamide | orange |
| 25 | 1-Methyl-3-acetyl-4-hydroxy-quinol-2-one | 3-Imino-isoindolinone | Cyanomethylthiocarb-butylamide | |
| 26 | 3-Acetyl-2,4-dihydroxy-quinoline | 3-Imino-4,5,6,7-tetra-chloro-isoindolinone | Cyanomethylthiocarb-butylamide | violet |
| 27 | 3-Acetyl-2,4-dihydroxy-quinoline | 3-Imino-5,6-dichloro-isoindolinone | Cyanomethylthiocarb-butylamide | Bordeaux red |
| 28 | 1-p-Tolyl-3-carbamoyl-4-formyl-pyrazol-5-one | 3-Imino-isoindolinone | Cyanomethylthiocarbamide | orange |
| 29 | 1-p-Tolyl-3-carbamooyl-4-formyl-pyrazol-5-one | 3-Imino-isoindolinone | Cyanomethylthiocarbanilide | red |
| 30 | 1-Phenyl-3-acetylamino-4-formyl-pyrazol-5-one | 3-Imino-isoindolinone | Cyanomethylthiocarbanilide | brown |
| 31 | 1-p-Chlorophenyl-3-carbamoyl-4-formyl-pyrazol-5-one | 3-Imino-isoindolinone | Cyanomethylthiocarbamide | orange |
| 32 | 1-p-Chlorophenyl-3-methyl-4-formyl-pyrazol-5-one | 4,6-Dimethoxy-5,7-dichloro-3-imino-iso-indolinone | Cyanomethylthiocarbamide | red |
| 33 | 1-p-Chlorophenyl-3-methyl-4-formyl-pyrazol-s-one | 5,6-Dichloro-3-imino-isoindolinone | Cyanomethylthiocarbamide | red |
| 34 | 3-Acetyl-2,4-dihydroxy-quinoline | 4,6-Dimethoxy-5,7-dichloro-3-imino-isoindolinone | Cyanomethylthiocarbamide | Bordeaux red |
| 35 | 3-Acetyl-4-hydroxy-coumarin | 4,6-Dimethoxy-5,7-dichloro-3-imino-isoindolinone | Cyanomethylthiocarbamide | red |

Example 36

25 parts of the pigment prepared according to Example 1, 100 parts of finely ground sodium chloride and 30 parts of diacetone-alcohol are initially introduced into a laboratory kneader with a capacity of 250 parts by volume. The mixture is kneaded for 5 hours, with cooling, and then introduced into 4,000 parts by volume of water. The sodium chloride and diacetone-alcohol dissolve and the pigment precipitates out. The suspension is filtered and the material on the suction filter is washed thoroughly with water and dried in a vacuum drying cabinet at 80°.

Example 37

1.09 g (0.005 mol) of 3-acetyl-2,4-dihydroxyquinoline-hydrazone and 1.31 g (0.00525 mol) of nickel acetate.4H₂O are suspended in 100 ml of dimethylformamide. After warming to 60° C., 1.78 g (0.005 mol) of 1-(cyano-α-naphthyl-thiocarbamoyl-methylene)-3-oxo-isoindoline, prepared from cyanothioacetic acid α-naphthylamide and 1-imino-3-oxo-isoindoline, are added, with stirring. The reaction mixture is heated to 120° C., with stirring, and stirred at the same temperature for 2 hours. It is then cooled to 100° C. and the metal complex which has precipitated out is filtered off, washed with dimethylformamide and ethanol and dried overnight at 80° C. in vacuo. 2.9 g (97% of theory) of a red metal complex of the formula

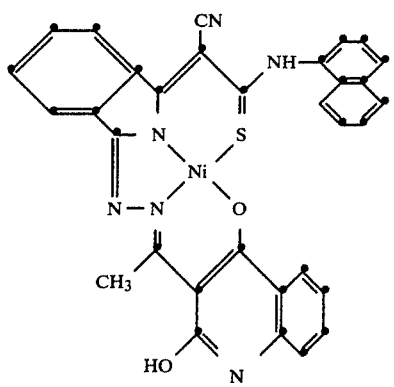

are obtained.

| Microanalysis: | C₃₁H₂₀N₆O₂SNi | MW 599 | | | |
|---|---|---|---|---|---|
| calculated: | 62.1% C | 3.4% H | 14.0% N | 5.4% S | 9.8 Ni |
| found: | 62.7% C | 3.7% H | 13.9% N | 5.7% S | 9.6% Ni |

The above metal complex colours plastics and surface coatings in red shades with excellent fastness properties.

Example (sic) 38–47

Analogously to Example 41, further 1:1 nickel complexes listed in Table 2, of the formula

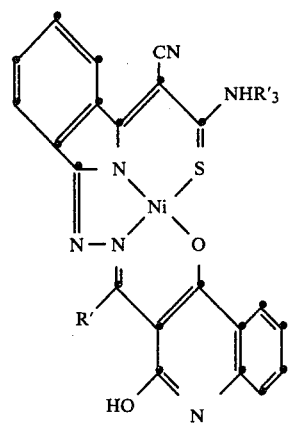

in which R' and R'₃ are as defined in column 2 or 3, are obtained by reacting an isoindolinone of the formula

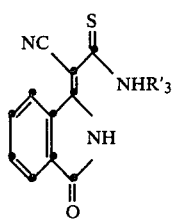

with a hydrazone of the formula

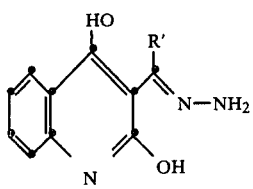

in the presence of nickel acetate.$4H_2O$.

| Example No. | R' | R'₃ | Shade in PVC |
|---|---|---|---|
| 38 | ⟨phenyl⟩ | H | red |
| 39 | " | ⟨phenyl⟩ | bluish red |
| 40 | $CH_3-$ | ⟨phenyl⟩–Cl | bluish red |
| 41 | " | ⟨phenyl⟩–$CF_3$ | bluish red |
| 42 | " | ⟨phenyl⟩–$NO_2$ | bluish red |
| 43 | $CH_3-$ | ⟨phenyl⟩–O–⟨phenyl⟩ | bluish red |
| 44 | " | ⟨phenyl⟩–$NHCOCH_3$ | bluish red |
| 45 | " | ⟨phenyl⟩–NHCO–⟨phenyl⟩–Cl | bluish red |
| 46 | " | –CO–⟨phenyl⟩ | bluish red |
| 47 | " | ⟨phenyl⟩ | red |

Example 48

21.74 g (0.1 mol) of 3-acetyl-2,4-dihydroxyquinoline-hydrazone and 26.11 g (0.105 mol) of nickel acetate. $4H_2O$ are suspended in 400 ml of ethylcellosolve and the suspension is warmed to 70° C. 22.93 g (0.1 mol) of the isoindolinone compound of the formula

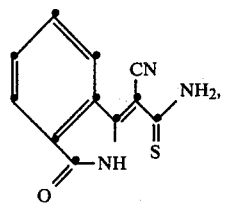

prepared from cyanomethylthiocarbamide and 1-imino-3-oxo-isoindoline, are then added and the mixture is heated to 110° C. It is stirred at the same temperature for 1½ hours and then cooled to 80° C. and filtered. The material on the suction filter is washed with ethylcellosolve and ethanol and dried overnight at 80° C. in vacuo. 48.2 g (99.3% of theory) of the 1:1 nickel complex of the formula

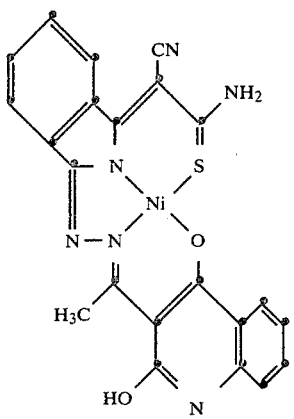

(only one of the possible isomeric or tautomeric forms has been considered) are obtained as a Bordeaux-red powder.

| Microanalysis: | $C_{22}H_{14}N_6O_2SNi$ | | Molecular weight 485.2 | |
| --- | --- | --- | --- | --- |
| calculated*: | 54.26% C  2.94% H | 17.26% N | 6.58% S | 12.06% Ni |
| found: | 54.0% C  3.0% H | 17.2% N | 6.6% S | 11.9% Ni |
| | 0.4 H₂O%.  (sic) | | | |

*calculated taking into account the amount of water found (0.4%)

The above metal complex colours plastics and surface coatings in Bordeaux-red shades with excellent fastness properties.

Example 49

65 parts of stabilised polyvinyl chloride, 35 parts of dioctyl phthalate and 0.2 part of the pigment obtained according to Example 36 are stirred with one another and then worked on a twin-roll mill for 7 minutes at 140°. A red-coloured sheet with very good fastness to light and migration is obtained.

Example 50

10 g of titanium dioxide and 2 g of the pigment prepared according to Example 1 are ground with 88 g of a mixture of 26.4 g of coconut alkyd resin, 24.0 g of melamine/formaldehyde resin (50% solids content), 8.8 g of ethylene glycol monomethyl ether and 28.8 g of xylene, for 48 hours in a ball mill.

If this surface coating is sprayed onto an aluminium foil, pre-dried for 30 minutes at room temperature and then stoved for 30 minutes at 120° C., a bluish red coating is obtained, which has good colour intensity and is distinguished by a very good fastness to overcoating, light and weather.

Example 51

4 parts of the finely divided pigment according to Example 36 are stirred into 20 parts of solvent of the following composition: 50 parts of Solvesso 150 (mixture of aromatic hydrocarbons), 15 parts of butyl acetate, 5 parts of Exkin II (ketoxime-based levelling agent), 25 parts of methyl isobutyl ketone and 5 parts of silicone oil (1% in Solvesso 150).

After complete fine dispersion has been reached (in about 15-60 minutes, depending on the type of stirrer), the binders are added, i.e. 48.3 parts of Baycryl L 530 (acrylic resin) (51&(sic) in xylene/butanol 3:1) and 23.7 parts of Maprenal TTX (melamine resin) (55% in butanol).

After a short period of homogenisation, the surface coating is applied by customary methods, such as spraying and dipping or, especially for the continuous coating of metal sheets, by the "coil-coating" process, and stoved (stoving: 30 minutes, 130°). The bluish red coatings obtained are distinguished by very good levelling, high gloss and excellent fine dispersion of the pigment, and also by excellent fastness to weather.

Example 52

If the procedure described in Example 36 is repeated, except that 2.78 parts of Staybelite Resin (HERCULES) are added to the kneading mixture, a pigment containing 10% of resin is obtained, which is distinguished by being easier to incorporate and by better dispersibility.

I claim:

1. A 1:1 metal complex of an azine of the formula

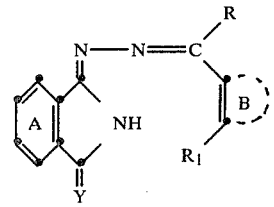

wherein ring A is unsubstituted or is substituted by two to four halogen atoms, by one or two alkyl of 1 to 4 carbon atoms, by one or two alkoxy of 1 to 4 carbon atoms, by phenyl, by phenoxy, by nitro, by benzoylamino or by alkanoylamino having 2 to 6 carbon atoms, R is hydrogen, alkyl of 1 to 4 carbon atoms, phenyl or naphthyl, B is phenylene, naphthylene, cyclohexenylene or a pyrazole, pyridine, pyrimidine, quinoline or coumarin radical, $R_1$ is OH or SH, Y is a radical of the formula

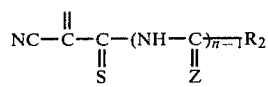

in which Z is an O or S atom, n is the number 1 or 2 and $R_2$ is an alkyl, aralkyl, cycloalkyl or aryl radical or an amino group which is unsubstituted or substituted by an alkyl, cycloalkyl, aralkyl or aryl radical, and the metal is selected from the group consisting of zinc, cadmium, manganese, cobalt, iron, copper and nickel.

2. A metal complex of the formula

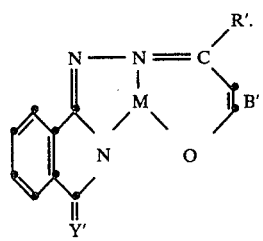

in which M is nickel or copper, R' is H or methyl, B' is a quinoline radical and Y' is a radical of the formula

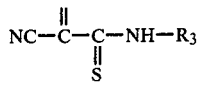

in which $R_3$ is an H atom, an alkyl group having 1-4 C or a radical of the formula

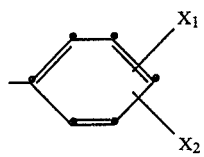

in which $X_1$ is an H, chlorine or bromine atom, a nitro, trifluoromethyl, carbamoyl or sulfamoyl group, an alkyl, alkoxy or alkylsulfamoyl group having 1-4 C, an alkanoylamino, alkylcarbamoyl or alkoxycarbonyl group having 2-6 C, or a phenoxy, phenylcarbamoyl or phenylsulfamoyl group which is unsubstituted or substituted by chlorine or bromine atoms or methyl groups, and $X_2$ is an H, chlorine or bromine atom or an alkyl or alkoxy group having 1-4 C.

3. A metal complex according to claim 1 wherein B is a quinoline radical.

4. A metal complex of the formula

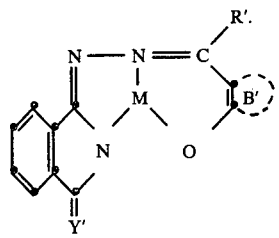

in which M is nickel or copper, R' is H or methyl, B' is a quinoline radical, and Y' is a radical of the formula $$NC-\overset{\|}{\underset{S}{C}}-\overset{\|}{\underset{Z}{C}}-NH-C-R_4$$

in which Z is an O or S atom and $R_4$ is an alkyl group having 1-4 C, a cyclohexyl group, a benzyl group or a group of the formula

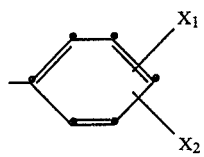

in which $X_1$ is an H, chlorine or bromine atom, a nitro, trifluoromethyl, carbamoyl or sulfamoyl group, an alkyl, alkoxy or alkylsulfamoyl group having 1-4 C, an alkanoylamino, alkylcarbamoyl or alkoxycarbonyl group having 2-6 C, or a phenoxy, phenylcarbamoyl or phenylsulfamoyl group which is unsubstituted or substituted by chlorine or bromine atoms or methyl groups, and $X_2$ is an H, chlorine or bromine atom or an alkyl or alkoxy group having 1-4 C.

5. A nickel complex according to claim 2 which has the formula

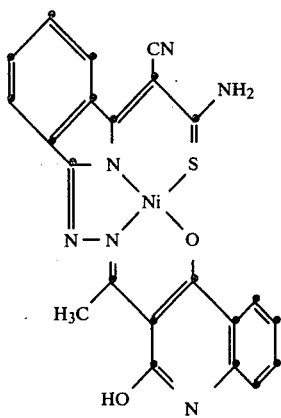

or is an isomer or tautomer thereof.